(12) United States Patent
Katz et al.

(10) Patent No.: US 8,072,596 B2
(45) Date of Patent: Dec. 6, 2011

(54) SYSTEM AND METHOD FOR ON-LINE ANALYSIS AND SORTING OF MILK COAGULATION PROPERTIES

(75) Inventors: Gil Katz, Doar-Na Emek HaYarden (IL); Or Shapira, Doar-Na Emek HaYarden (IL); Liubov Lemberskiy-Kuzin, Haifa (IL); Niv Pinsky, Doar-Na Emek HaYarden (IL)

(73) Assignee: S.A.E. Afikim Milking System Agricultural Cooperative Ltd, Kibbutz Afikim (IL)

( * ) Notice: Subject to any disclaimer, the term of this patent is extended or adjusted under 35 U.S.C. 154(b) by 492 days.

(21) Appl. No.: 12/078,999

(22) Filed: Apr. 9, 2008

(65) Prior Publication Data

US 2009/0255473 A1    Oct. 15, 2009

(51) Int. Cl.
   *G01J 3/42* (2006.01)
   *A01J 5/007* (2006.01)
(52) U.S. Cl. ..... 356/319; 356/72; 119/14.01; 119/14.14
(58) Field of Classification Search .... 119/14.01–14.55; 356/51, 73; 426/33–41, 231
See application file for complete search history.

(56) References Cited

U.S. PATENT DOCUMENTS

| | | | |
|---|---|---|---|
| 3,082,738 A * | 3/1963 | Golay | 119/14.46 |
| 2003/0098969 A1* | 5/2003 | Katz et al. | 356/73 |
| 2008/0000426 A1* | 1/2008 | Grabek et al. | 119/14.14 |

FOREIGN PATENT DOCUMENTS

| | | |
|---|---|---|
| DE | 19516615 | 10/1996 |
| WO | WO 03/040704 | 5/2003 |
| WO | WO 2006/110963 | 10/2006 |
| WO | WO 2009/125386 | 10/2009 |

OTHER PUBLICATIONS

International Preliminary Report on Patentability Dated Jul. 21, 2010 From the International Preliminary Examining Authority Re.: Application No. PCT/IL2009/000324.
Fagan et al. "On-Line Prediction of Cheese Making Indices Using Backscatter of Near Infrared Light", International Dairy Journal, XP002547214, 18(2): 120-128, Feb. 2008.
Herbert et al. "Fluorescence Spectroscopy Investigation of Acid- or Rennet-Induced Coagulation of Milk", Journal of Dairy Science, XP002547213, 82(10): 2056-2062, Oct. 1999.
Laporte et al. "The Near-Infrared Optic Probe for Monitoring Rennet Coagulation in Cow's Milk", International Dairy Journal, XP002547215, 8(7): 659-666, Jul. 1998.

(Continued)

*Primary Examiner* — Tarifur Chowdhury
*Assistant Examiner* — Tara S Pajoohi
(74) *Attorney, Agent, or Firm* — Pearl Cohen Zedek Latzer, LLP

(57) ABSTRACT

A method for on-line channeling of milk based on predicted coagulation properties where the method comprises sampling raw milk from a milk line between a milking station and a collection point, performing spectral analysis of one or more of optical transmission, optical reflectance, scatter and fluorescence on the raw milk sample, predicting at least one coagulation parameter on-line based on the spectral analysis, and channeling milk from the milking station on-line to one of a plurality of destinations based on the at least one coagulation parameter.

49 Claims, 8 Drawing Sheets
(2 of 8 Drawing Sheet(s) Filed in Color)

OTHER PUBLICATIONS

International Search Report and the Written Opinion Dated Oct. 15, 2009 From the International Searching Authority Re.: Application No. PCT/IL2009/000324.

Response Dated Feb. 9, 2010 to Written Opinion of Oct. 15, 2009 From the International Searching Authority Re.: Application No. PCT/IL2009/000324.

Emmons et al. "Cheese Yield Experiments and Proteolysis by Milk-Clotting Enzymes", Journal of Dairy Science, 73: 2028-2043, 1990.

Emmons et al. "Predictive Formulas for Yield of Cheese From Composition of Milk: A Review", Journal of Dairy Science, 73: 1365-1394, 1990.

Kübarsepp et al. "A Comparison of the Methods for Determination of the Rennet Coagulation Properties of Milk", Acta Agriculturae Scandinavica, Section A—Animal Sciences, 55(4): 145-148, 2005.

Riddell-Lawrence et al. "Effect of Curd Firmness on Stirred Curd Cheese Yield", Journal of Dairy Science, 72: 313-321, 1989.

Kübarsepp et al. "A Comparison of the Methods for Determination of the Rennet Coagulation Properties of Milk", Acta Agriculturae Scandinavica, Section A—Animal Sciences, XP009120636, 55(4): 145-148, Dec. 1, 2005.

* cited by examiner

SYSTEM AND METHOD FOR ON-LINE ANALYSIS AND SORTING OF MILK COAGULATION PROPERTIES

FIELD OF THE INVENTION

The present invention, in some embodiments thereof, relates to the field of quantitative analysis of milk and, more particularly, but not exclusively, to quantitative analysis of coagulation properties of milk.

BACKGROUND OF THE INVENTION

The coagulation properties of milk supplied by the dairies are of great importance to the cheese industry. Milk with favorable coagulation characteristics, e.g. short coagulation time and high curd firmness, may produce higher cheese yield with a desirable composition as compared to milk with less favorable properties.

In the article "Review of systems for monitoring curd setting during cheesemaking" by O'Callaghan et al., published in the Journal of Dairy Technology, Vol. 55, No. 2, May 2002, pp. 65-74, which is incorporated herein by reference in its entirety, known methods for detecting coagulation properties of milk are described. The methods described are based on physiochemical changes that occur in milk during rennet coagulation. Typically, rennet is added to milk samples extracted from a general collection tank in a dairy and coagulation properties of the coagulating milk are measured.

In the article "A comparison of the methods for determination of the rennet coagulation properties of milk", by KÜBARSEPP et al, published in Acta Agriculturae Scand Section A, 2005; Vol. 55: pp. 145-148, which is incorporated by reference in its entirety, there is described two known technologies for measuring coagulation properties: the formagraph and the optigraph.

According the article by KÜBARSEPP et al., the formagraph measures tiny forces exerted by a pendulum when samples of coagulating milk are exposed to linear oscillations. The recorded measurements are firmness and time. Firmness is typically defined as a combination of viscosity and elastic characteristics of the coagulating milk.

According the article by KÜBARSEPP et al., the optigraph is based on measuring Near InfraRed (NIR) signal attenuation emitted from the coagulating milk as the coagulation process develops.

Both methods require adding enzyme prior to performing the measurement and are therefore destructive. The analysis duration of these methods may be longer than the milking session and are therefore are implemented for evaluation of the milk at a dairy in the general tank.

International Patent Application Publication WO03040704 entitled "Spectroscopic Fluid Analyzer" which is incorporated herein by reference in its entirety, describes an NIR spectroscopy fluid analyzing system for determining concentrations of component parts of fluid. The system uses a series of Light Emitting Diodes (LEDs) for illuminating a sample of fluid and photo-detectors for measuring the transmission absorbance through the sample and the reflectance or scattering from the sample for the wavelength range of each LED. The concentration of component parts of the sample is expressed in the form of a polynomial which is a function of the measured transmitted and/or reflected intensities, and of empirical coefficients, which are extracted by prior statistical analysis on measured intensities obtained from a large number of test samples having known concentrations of the component. Also described in WO03040704 is a sample chamber capable of being used to perform optical absorption measurements on a flowing sample of fluid.

SUMMARY OF THE INVENTION

According to an aspect of some embodiments of the present invention, there is provided a method and apparatus for on-line and/or real-time analysis of at least one coagulation property of raw milk collected in a milk parlor.

According to an aspect of some embodiments of the present invention, there is provided a method and apparatus for on-line and/or real-time milk channeling based on on-line detection of at least one coagulation parameter of raw milk collected in a milk parlor.

According to an aspect of some embodiments of the present invention there is provided a method for on-line channeling of milk based on predicted coagulation properties, the method comprising sampling raw milk from a milk line between a milking station and a collection point, performing spectral analysis of one or more of optical transmission, optical reflectance, scatter and fluorescence on the raw milk sample, predicting at least one coagulation parameter on-line based on the spectral analysis, and channeling milk from the milking station on-line to one of a plurality of destinations based on the at least one coagulation parameter.

Optionally, the spectral analysis is implemented with NIR spectroscopy.

Optionally, the spectral analysis is implemented with visible light spectroscopy.

Optionally, the spectral analysis is performed using a plurality of LED, each configured for illuminating the raw milk sample at a different wavelength within the range to be used for the measurement.

Optionally, the range is between 365 nm to 950 nm.

Optionally, the spectral analysis is performed using one or more detectors to detect light transmitted through the raw milk sample.

Optionally, the spectral analysis is performed using one or more detectors to detect light reflected from the raw milk sample.

Optionally, the spectral analysis is performed using one or more detectors to detect light scatter from the raw milk sample.

Optionally, the spectral analysis is implemented with fluorescence spectroscopy.

Optionally, the spectral analysis is performed using a plurality of light sources having pre-selected wavelengths between 290 nm and 430 nm.

Optionally, the method comprises detecting light scattered at substantially 90 degrees.

Optionally, prediction is based on pre-stored empirical data.

Optionally, the method comprises determining a coagulation property of the raw milk sample based on a pre-defined polynomial including empirical coefficients obtained from statistical analysis of a large number of test samples from different cows and from different periods over a milking session having a known coagulation property.

Optionally, the known coagulation property is determined from optical measurements of each of the test samples after adding rennet to the test sample.

Optionally, the sampling is performed on pulsating milk flow.

Optionally, the spectral analysis is performed a plurality of times on each sample.

Optionally, the coagulation parameter is selected form a group including: Cy(90), Cy(60), and RCT.

Optionally, the analysis on the raw milk sample does not involve adding a coagulant to the milk.

Optionally, the channeling is performed automatically and without human intervention.

Optionally, the channeling is performed for milk station of an individual cow.

According to an aspect of some embodiments of the present invention there is provided a system for on-line channeling of milk according to a predicted coagulation property of raw milk comprising a milk line configured to provide milk flow between a milking station and a collection point, a sampling chamber configured for receiving pulsating milk samples from the milk line, an analyzer configured for determining at least one optical property of a sample of raw milk flowing through the milk line, a processor operative to estimate a coagulation property of the milk based on the optical data, and a controller that receives the estimate from the processor and channels the milk in the flow line to a destination responsive to the estimated coagulation property.

Optionally, the analyzer is an NIR spectroscopy analyzer.

Optionally, the analyzer includes a visible light spectroscopy analyzer.

Optionally, the analyzer is a fluorescence spectroscopy analyzer.

Optionally, the system comprises a memory unit for storing empirical coefficients relating output from the analyzer to at least one coagulation property of the sample based on a defined polynomial function.

Optionally, the empirical coefficients are obtained from statistical analysis of a large number of test samples from different cows and from different periods over a milking session having a known coagulation property.

Optionally, the coagulation property is determined from a parameter selected from the group comprising: Cy(90), Cy(60), and RCT.

Optionally, the controller is configured for channeling milk determined to have curd firmness below a defined threshold for drinking and channeling milk determined to have curd firmness above the defined threshold for cheese production.

Optionally, the controller is configured for channeling milk at a resolution of each pulsating sample of milk.

Optionally, the controller is configured for channeling milk at a resolution of approximately once every 2 seconds.

Optionally, the analyzer is configured for performing analysis on the without adding a coagulant to the sample of raw milk.

According to an aspect of some embodiments of the present invention there is provided a method for predicting coagulation properties of raw milk, the method comprising performing spectral analysis of one or more of optical transmission, optical reflectance, scatter and fluorescence on the raw milk sample without adding a coagulant, and predicting at least one coagulation parameter based on the spectral analysis.

Optionally, the spectral analysis is implemented with NIR spectroscopy.

Optionally, the spectral analysis is implemented with visible light spectroscopy.

Optionally, the spectral analysis is implemented with fluorescence spectroscopy.

Optionally, prediction is based on pre-stored empirical data.

Optionally, the predicting is based on a pre-defined polynomial including empirical coefficients obtained from statistical analysis of a large number of test samples from different cows and from different periods over a milking session having a known coagulation property.

Optionally, the known coagulation property is determined from optical measurements of each of the test samples after adding rennet to the test sample.

Optionally, the spectral analysis is performed a plurality of times on each sample.

Optionally, the coagulation parameter is selected form a group including: Cy(90), Cy(60), and RCT.

According to an aspect of some embodiments of the present invention there is provided a system for on-line analysis of at least one coagulation property of milk comprising a sampling chamber configured for receiving pulsating milk samples on-line from the milk line, an analyzer configured for determining at least one property of a milk sample in the sampling chamber, and a processor operative to estimate on-line a coagulation property of the milk sample based on the at least one property and pre-stored empirical data relating the at least one property to a coagulation property of the milk.

Optionally, the analyzer is configured for performing analysis on the without adding a coagulant to the sample of raw milk.

Optionally, the analyzer is configured for determining at least one optical property of the milk sample.

Optionally, the coagulation property is determined by a parameter selected from the group comprising: Cy(90), Cy(60), and RCT.

Optionally, the system comprises a memory unit for storing empirical coefficients relating output from the analyzer to at least one coagulation property of the milk sample based on a defined polynomial function.

Optionally, the empirical coefficients are obtained from statistical analysis of a large number of milk samples from different cows and from different periods over a milking session having a known coagulation property.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic drawing of an exemplary system for on-line analysis and channeling of raw milk based on coagulation properties according to some embodiments of the present invention;

FIG. 2 is an exemplary diagram of an optical measurement system that can be implemented for on-line analysis of raw milk to determine coagulation properties according to some embodiments of the present invention;

FIG. 3 is simplified flow chart describing an exemplary method for determining relationship between detected intensities from a NIR spectroscopy measurement system and at least one coagulant property of raw milk according to some embodiments of the present invention;

FIG. 4 is a schematic diagram a fluorescence measurement system to be used for on-line analysis of coagulation properties of raw milk according to some embodiments of the present invention;

FIG. 5 is a simplified flow chart describing an exemplary method for determining a relationship between detected emissions from a fluorescence measurement system and at least one coagulant property of raw milk according to some embodiments of the present invention;

FIG. 6 is a simplified flow chart describing an exemplary method for on-line analysis and channeling of raw milk based on coagulation properties according to some embodiments of the present invention;

Figure 7:
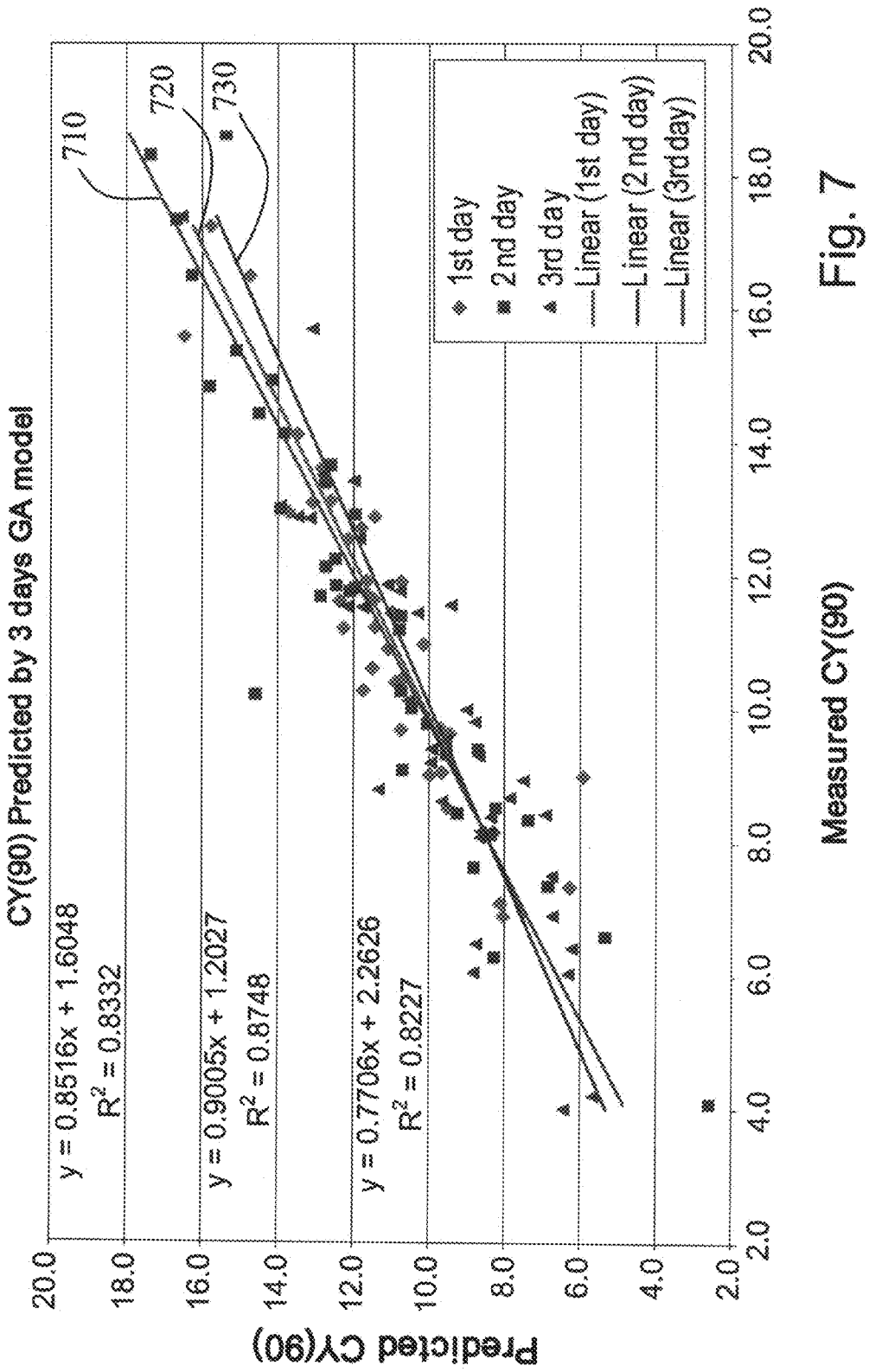
Figure 8A:
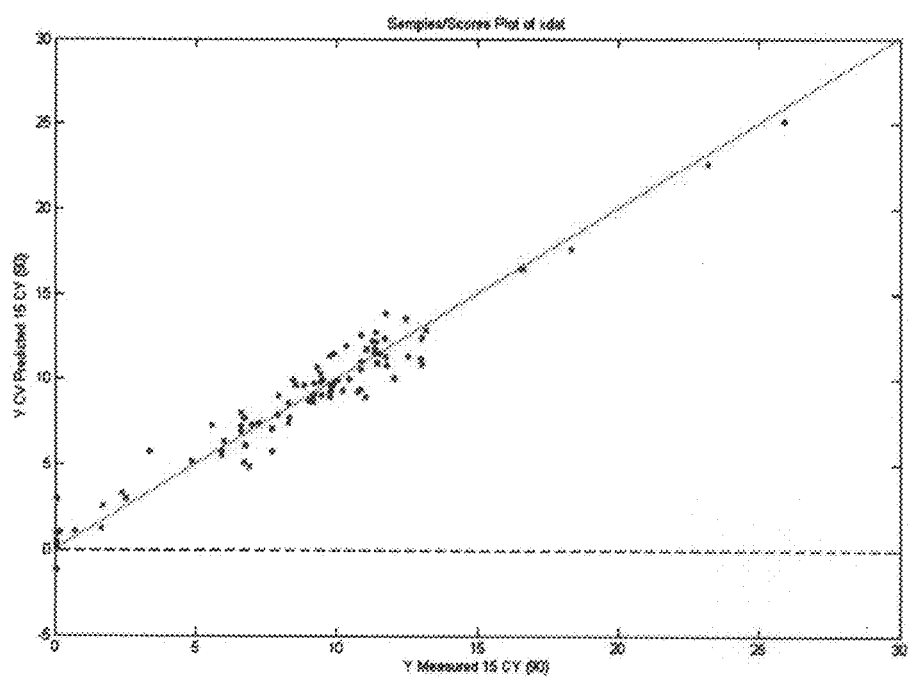
Figure 8B:
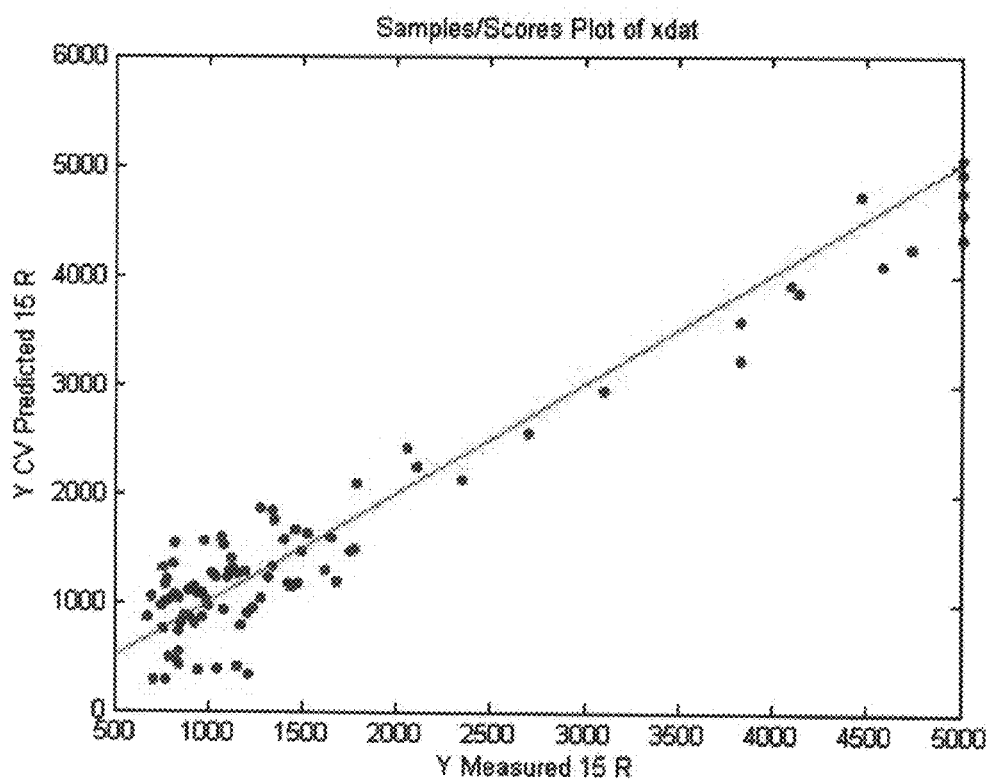

FIG. 7 is a graph showing sample results obtained from three different polynomials used to predict values of curd firmness using an on-line NIR spectroscopy system according to some embodiments of the present invention; and FIGS. 8A and 8B are graphs showing sample results obtained when comparing measured and predicated values of curd firmness and rennet coagulation time respectfully for values predicted with an on-line fluorescence system according to some embodiments of the present invention.

DESCRIPTION OF SPECIFIC EMBODIMENTS OF THE INVENTION

The present invention, in some embodiments thereof, relates to the field of quantitative analysis of milk and, more particularly, but not exclusively, to quantitative analysis of coagulation parameters of milk.

There is a significant variation in milk coagulation properties between different cows and during the milking session of an individual cow. Quantitative analysis of coagulation parameters of milk allows selecting milk according to its suitability for desired products, e.g. cheese production, milk for drinking. With known technologies for measuring coagulation parameters of milk, coagulation properties may be determined for the average yield of the farm based on analysis of coagulating milk. Milk may be distributed to different destination based on the properties determined for the average yield.

The present inventors have found that in order to improve milk sorting according to its coagulation properties, on-line and/or real time analysis of coagulation parameters may be implemented. The inventors have found that such analysis facilitates on-line channeling milk to different tanks, based on the coagulation properties of individual cows and/or based on changes of the coagulation parameters during a milking session. Improving the resolution by which milk is separated according to its suitability for desired products may enhance the economic value of the average milk of the herd. As used herein the terms on-line and/or real time analysis of coagulation parameters refers to analysis that is performed during the milking session such that the results of the analysis are obtained in time to affect channeling milk flow possessing the determined parameters to a specified destination, e.g. without hindering the milk flow through the milk lines.

Typically, fat concentration of milk increases in an approximately linear fashion during a milking session. Since fat is among the solids that coagulate, the coagulation ability of milk is also expected to increases during the progression of the milking session. However, if 'over milking' occurs, e.g. the milking session extends beyond a desired period, the coagulation ability of milk typically decreases due to exhaustion of the empty teat.

Furthermore, it is known that there are typically one or more cows in a herd at any given time that may be infected with bacteria that serve to destroy and/or impair coagulation ability of their milk. Diagnosis is typically by detection of elevated Somatic Cell Count (SCC) in the cow's milk. Early diagnosis of an infected cow may prevent spreading of the bacteria among the other cows in the herd. The present inventors have found that on-line analysis of coagulation parameters as it is being collected facilitates identifying infected cows during each milking session so that the infected cows may be immediately treated. The present inventors have found that low coagulation ability of milk due to infection, e.g. due to a high SCC, may typically be detected in the beginning of the milking session since the somatic cells tend to concentrate in the bottom of the teat.

An aspect of some embodiments of the present invention provides a system for on-line analysis of coagulation properties of raw milk. According to some embodiments of the present invention, the system includes at least one measuring chamber operative to accept a fluid sample, one or more NIR light sources operative to illuminate fluid flowing through the measuring chamber, and one or more NIR light detectors operative to detect transmission absorption, reflectance and/or scattering of light from a flowing fluid. According to some embodiments of the present invention the NIR light sources include a series of LED, each have a different wavelength.

According to other embodiments of the present invention, the system includes at least one measuring chamber operative to accept a fluid sample, one or more light sources with a pre-selected wavelength between 290 nm and 430 nm for excitation of milk samples, and a spectrometer for recording fluorescence emission spectra.

An aspect of some embodiments of the present invention provides a method for on-line analysis of one or more coagulation properties of raw milk based on spectroscopic fluid analysis. In some exemplary embodiments measured intensities of transmitted, reflected, scattered and/or absorbed NIR light are compared to measured intensities obtained from a large number of test samples having known coagulation properties. In other embodiments fluorescence emission spectra are compared to measured emissions obtained from a large number of test samples having known coagulation properties.

According to some embodiments of the present invention, one or more coagulation properties of raw milk are expressed in the form of polynomial expressions that are functions of the measured emissions, transmitted, reflected, scattered, and/or absorbed intensities, and of empirical coefficients. According to embodiments of the present invention in order to define the empirical coefficients, data are obtained from absorption and reflectance measurements made on samples of milk taken from numerous cows and over the course of a milking session using the system and methods described herein. In addition, the coagulation properties of each sample of milk are independently determined, using known methods. These known coagulation properties are then used to extract the empirical coefficients by using statistical analysis methods described herein.

According to some embodiments of the present invention, empirical coefficients are determined for each light source (each having a different wavelength) and for each of the photo-detectors measuring detected light, e.g. emitted, transmitted, reflected and/or scattered.

According to some embodiments of the present invention the empirical coefficients are extracted, for example by performing a Partial Least Squares (PLS) regression, Partial Component Analysis (PCA) and/or multivariate component analysis on measured intensities, obtained by measuring large number of test samples having known coagulation properties. Once extracted, the coefficients are stored, along with the coagulation properties of the sample with which they are associated, as a reference database in memory for use in measurements of unknown samples. According to embodiments of the present invention, measured values are compared to contents of the database employing methods similar to chemometric analysis methods used in the analysis of multiple component chemical reaction dynamics.

According to some embodiments of the present invention, the one or more coagulation parameter includes curd firmness, e.g. expected curd firmness one hour after adding rennet Cy(60) and/or ninety minutes after adding rennet Cy(90). In some exemplary embodiments, milk with relatively high curd firmness is channeled to a tank for dry cheese production. In some exemplary embodiments of the present invention, milk with relatively low curd firmness is channeled to a tank where the milk will be packaged for drinking According to some embodiments of the present invention, the one or more coagulation properties include Rennet Coagulation Time (RCT). In some exemplary embodiments, milk with relatively fast RCT is channeled to a tank for dry cheese production while milk with a relatively slow RCT may be channeled for drinking.

An aspect of some embodiments of the present invention provides a system for channeling milk to different collection vats based on on-line analysis of one or more coagulation parameters of the raw milk as it is being collected. According to some embodiments of the present invention, the system includes an analyzer for performing on-line analysis of samples of raw milk collected and a selector valve for channeling milk flow through a selected milk line leading to the selected milk collection valve. According to some embodiments of the present, selector valve is operative to channel milk through one or more milk lines during a single milking session of an individual cow. According to some embodiments of the present invention, the system includes a controller for controlling the function of the selector valve based on data output from the analyzer.

Figure 1:
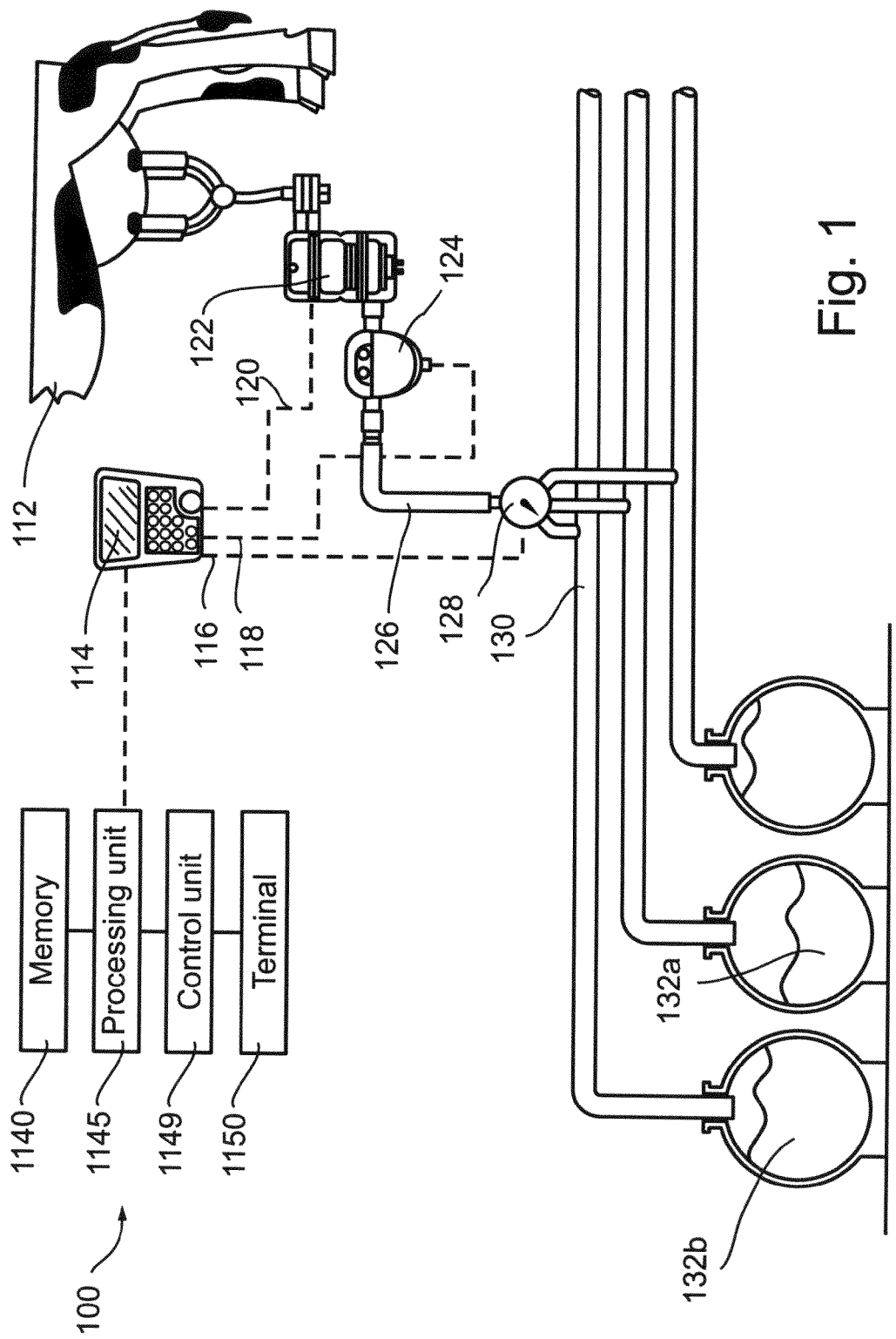

Reference is now made to FIG. 1 showing an exemplary system for on-line coagulation analysis of raw milk and channeling based on detected coagulation properties according to some embodiments of the present invention. According to some embodiments of the present invention, milk analysis and channeling system 100 is stationed in a milking parlor and is implemented for analyzing and channeling milk pumped from individual cows during each milking session. According to some embodiments of the present invention, milk pumped from a cow 112 flows through a milk meter 122, a raw milk coagulant analyzer 124 and through a selector valve 128 that channels the milk through one or more milk lines 130 into collection vats 132, e.g. collection vats 132A, 132B. According to some embodiments of the present invention, on-line analysis of coagulation properties is performed by analyzer 124 and values and/or signals obtained from analyzer 124 are transmitted to a controller system 114. Typically, controller system 114 controls function of selector valve 128 based on obtained data and thereby controls channeling of milk flow to the different milk lines 130 based on one or more measured parameters.

According to some embodiments of the present invention, communication between controller system 114 and optional milk meter 122, coagulant analyzer 124, and selector valve 128 may be by tethered lines 120, 118, and 116 respectfully. Optionally, milk meter 122, coagulant analyzer 124, and selector valve 128 are also powered through tethered lines 120, 118, and 116. Optionally, communication and/or powering are achieved by wireless communication, e.g. Bluetooth communication. Optionally one or more of controller system 114, milk meter 122, coagulant analyzer 124, and selector valve 128 are integrated into a single unit.

According to some embodiments of the present invention, coagulant analyzer 124 is an NIR spectroscopy analyzer. In some exemplary embodiments, coagulant analyzer may be similar to the NIR spectroscopic milk analyzer described in incorporated International Patent Publication No. WO 03/040704. According to other embodiments of the present invention, coagulant analyzer 124 is a fluorescence analyzer based on detecting fluorescence emission spectra of milk samples. In one exemplary embodiment, analyzer 124 includes more than one analyzer, e.g. an NIR spectroscopy analyzer and a fluorescence analyzer.

According to some embodiments of the present invention, coagulant analyzer 124 is implemented to determine, sense and/or measure one or more parameters related to coagulation, e.g. RCT, Cy(60) and/or Cy(90). In some exemplary embodiments, coagulation analyzer 124 is also implemented to determine other properties of milk, e.g. levels of component parts of milk as described in incorporated International Patent Publication No. WO 03/040704.

According to some embodiments of the present invention, controller system 114 includes a memory 1140, a processor 1145 and a controller 1149. Optionally, control system 114 communicates with a computing system so that at least part of the processing and memory functionality is provided by the computing system. According to some embodiments of the present invention, signals, data and/or values obtained from analyzer 124 and/or milk meter may be at least partially processed by control system 114. Optionally processing of data is performed by analyzer 124 and/or milk meter 122. According to some embodiments of the present invention, memory 1140 is implemented to store one or more threshold values based on which selection of the milk line through which milk is to flow is based. According to some embodiments of the present invention, memory 1140 is implemented to store a plurality of coefficients defining one or more polynomials by which coagulation properties of raw milk is expressed as a function of data obtained from analyzer 124. According to some embodiments of the present invention, analyzer 124 includes processing and/or memory capability to store and/or determine one or more polynomial coefficients and/or threshold values.

According to some embodiments of the present invention control system 114 is provided with a terminal 1150 having a display and a user input unit for user interface with the milk analysis and channeling system 100. In some exemplary embodiments, a user, through interface with control system 114, can select and/or adjust the number of activated milk lines 130 through which selector valve 128 may channel milk and/or the specific channel and/or vat through which milk should be directed. In some exemplary embodiments, a user, through user interface with control system 114, can select and/or adjust one or more parameter values used to determine the destination of pumped milk. Other parameters may be selected and/or adjusted by the user though user interface unit of control system 114, e.g. duration of milking session, sampling rate of analyzer 124. According to embodiments of the present invention, control system 114 is implemented to receive cow check-in information, e.g. through user interface unit. Cow check-in information may include identification of cow, milk session number per day, nutritional information of the cow, health status of the cow, etc. According to some embodiments of the present invention, control system 114 is implemented to report information regarding the milking session and measured parameters. Generally, the diversion and/or channeling of the milk are performed automatically. According to some embodiments of the present invention, control system 114 is replaced by an Input/Output (I/O) device and/or is integrated into a central control system.

According to embodiments of the present invention selector valve can be any known selector and/or diverting valves applicable with the dairy industry in terms of: material, flow rate & self cleaning ability. In some exemplary embodiments, the average flow rate in the milking line is approximately 5 lit/min of milk and 10 lit/min of air with approximate maximum values of 15 lit/min milk flow.

Although in FIG. 1 milk meter 122 is shown to be upstream from analyzer 124, analyzer 124 may be positioned upstream of milk meter 122 and/or may be integrated with milk meter 122. Although the system is described for milk channeling of individual cow output it can be equally applied to a common milk line from a number of cows.

Figure 2:
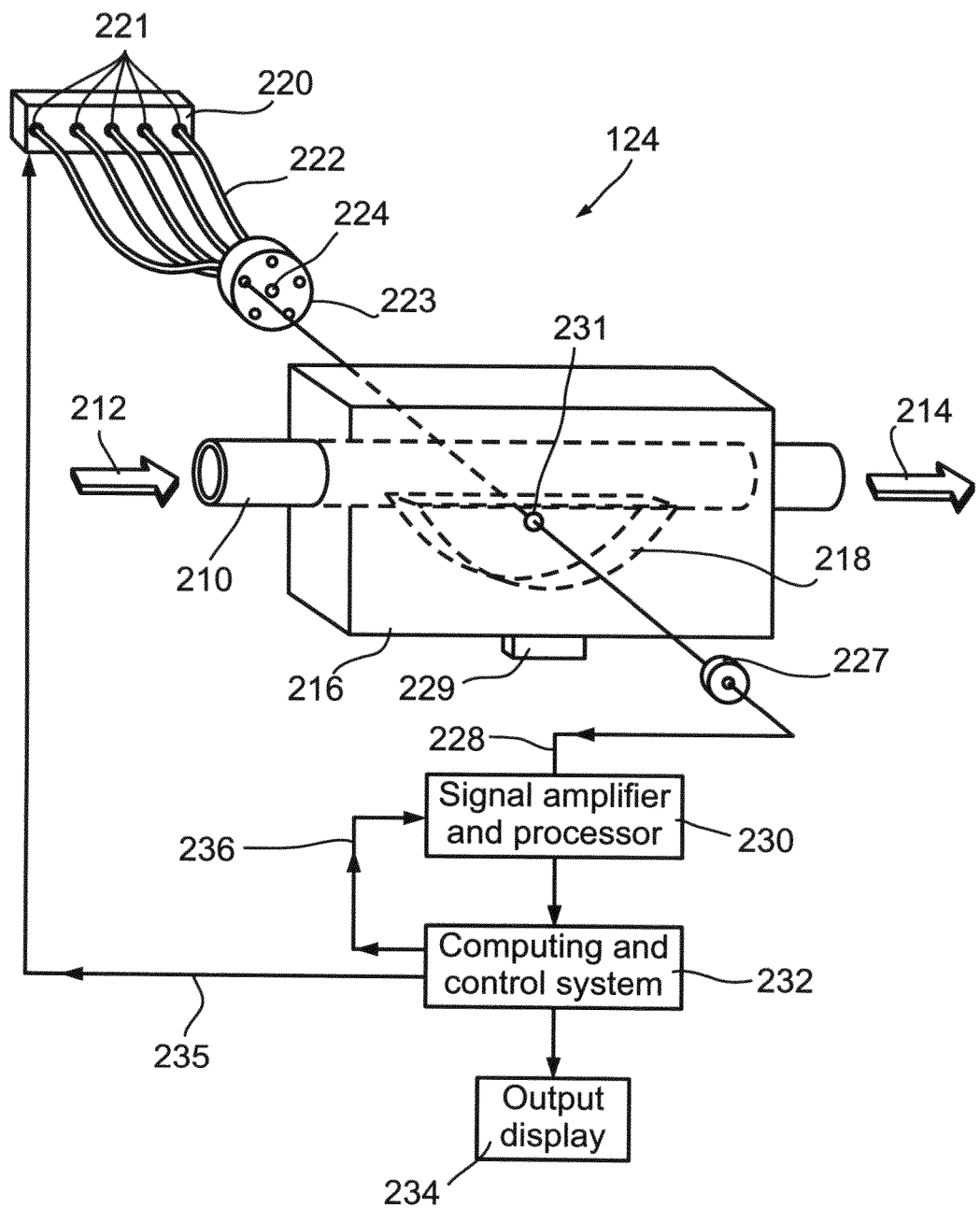

Reference is now made to FIG. 2 showing an exemplary diagram of an optical measurement system that can be implemented for on-line analysis of raw milk to determine coagulation properties according to some embodiments of the present invention. According to some embodiments of the present invention, the optical analysis system shown in FIG. 2 is similar to the optical analysis system described in incorporated International Patent Publication No. WO03040704 but includes a computing and control system 232 suitable for computing coagulation related parameters.

According to embodiments of the present invention, analyzer 124 is integrated along a flow conduit, pipe and/or tube 210 between a milking station 212 and a collection point 214. According to some embodiments of the present invention, analyzer 124 includes a sampling chamber 216 to which milk from tube 210 is collected in sample cavity 218 and analyzed. In some exemplary embodiments, sampling chamber 216 has a recessed cavity 218, preferably adjoining the main flow conduit of the milk, and located in a generally downwards direction, such that it fills with a constantly changing sample of the flowing milk. This enables optical transmission measurements to be performed on a pulsating milk flow, without the pulsation and turbulence significantly affecting the accuracy of the measurement.

According to some embodiments of the present invention, optical transmission measurements are performed using an LED array 220 which incorporates a number of discrete LED emitters 221, each emitting at a different wavelength within the range to be used for the measurement. According to an exemplary embodiment, the wavelengths of the LED's 221 range between 365 nm to 950 nm, to cover the visible to NIR regions of the spectrum. Optionally, light output from each LED 221 is transmitted by means of an optical fiber 222 to a rosette 223, where all fibers 222 are bundled together to form a compact source, which emits the wavelength of whichever LED, or LEDs 221 are illuminated. In some exemplary embodiments a detector 224 is positioned in the center of rosette 223 to detect reflected and/or backscattered light from LED array 220.

According to some embodiments of the present invention, the light transmitted from source rosette 223 enters through an entry port and passes through sample cavity 218 to be emitted through one or more exit ports 231 to be detected, optionally by means of a silicon photo-detector 227 disposed adjacent to exit port 231. In some exemplary embodiments, a detected signal 228 corresponding to the beam intensity is input into signal amplification and processing system 230. The output intensities from the detection system may be fed to a computing and control system 232, where the spectra obtained are analyzed by methods described herein. In some exemplary embodiments, computing and control system 232 passes control information 235 to LED sources 221, to provide the modulation frequency, if used, and which is also input by means of control line 236 to the phase sensitive detector in the signal amplifying and processing system 230. Computing and control system 232 may also be implemented to control the switching order and timing of LED sources 221, for scanning the complete spectral range to be measured.

According to an exemplary embodiment, each LED 221 is turned on for several milliseconds, and the absorption and/or scattering measurements are performed at that wavelength. In order to perform the measurements more rapidly, the transmission absorbance signal on detector 227 and the backscattering signal on detector 224 may be measured simultaneously. According to some embodiments, a traverse detector 229 is used to measure light scattered at substantially 90 degrees (or placed at some other angle intermediate between 0 and 180 degrees relative to the laser beam direction to measure scatter in that direction), and its signal is also measured simultaneously with the signals on detectors 224 and 227.

Typically, the pulse rate of the milk flow through chamber 216 during milking is at most generally no faster than one milk pulse every two seconds. Since this repetition rate is generally significantly slower than the measurement scan rate, the absorbance/scattering measurements may be repeated several times on each milk sample collected in sample cavity 218, and then averaged for each sample, thereby reducing the variance level of the measurements and increasing the accuracy with which the concentrations can be calculated.

Figure 3:
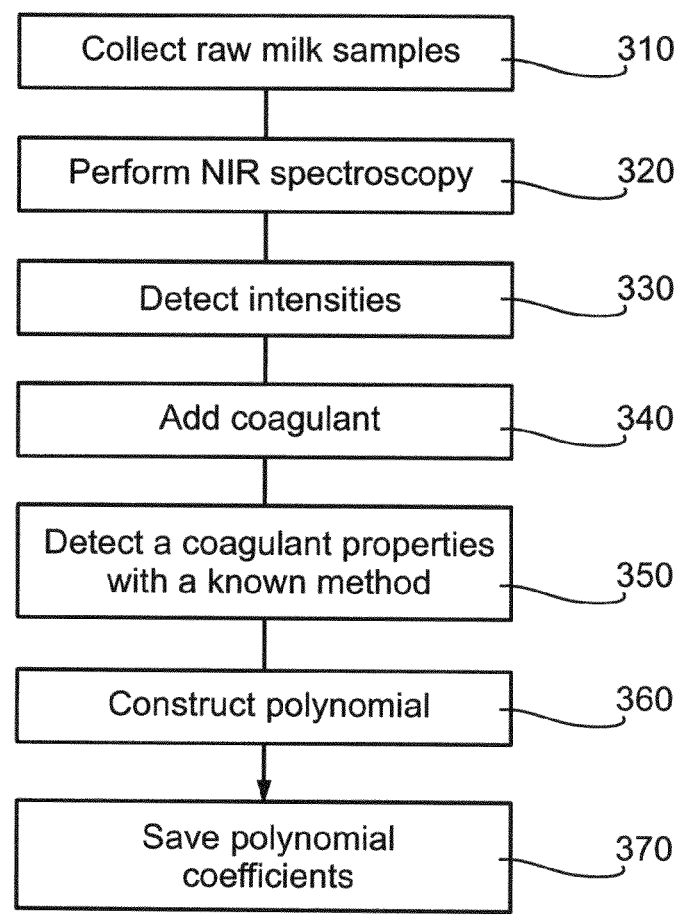

Reference is now made to FIG. 3 showing a simplified flow chart describing an exemplary method for determining relationship between detected intensities from a NIR spectroscopy measurement system and at least one coagulant property of raw milk according to some embodiments of the present invention. According to some embodiments of the present invention, raw milk samples are collected from a large number of cows and from different points in time during the milking session (block 310). According to some embodiments of the present invention NIR spectroscopy according to methods described herein and/or in incorporated International Patent Publication WO03040704 (block 320). One or more detected intensities from the NIR spectroscopy are detected, e.g. reflected intensities, transmitted intensities, back-scattered intensities (block 330). In some exemplary embodiments, a coagulation, e.g. rennet, is added to each of the samples collected (block 340). One or more known methods for determining one or more coagulant property may be determined (block 350). In one example, a curd firmness parameter is determined using an optigraph. For example curd firmness after 90 minutes, Cy(90) is determined. In one example the parameter RCT is determined using known methods. More than one parameter may be determined and more than one known method may be implemented to determine each of the parameters.

According to some embodiments of the present invention, coagulation properties of raw milk is defined by fitting the intensity of the optical beam transmitted through the fluid and of the beam reflected and/or scattered from the fluid to a polynomial expression for a defined coagulation parameter in terms of the intensities detected and one or more empirical coefficients (block 360). According to embodiments of the present invention, empirical coefficients are determined by a statistical analysis of transmitted, reflected and/or scattered intensities obtained from a plurality of samples of the fluid having known coagulation parameters. Once determined, the empirical coefficients are preferably stored in a database (block 370) and may be used to determine coagulation parameters of future samples of raw milk in real time.

According to some embodiments of the present invention, a polynomial expression is defined in terms of the measured transmitted, reflected and/or scattered light intensities for each LED measurement is used. In some exemplary embodiment, each intensity term appears with an empirical coefficient so that the polynomial may be of the form:

$$CP = \Sigma ax_{tj}I_{tj} + \Sigma bx_{tj}I^2_{tj} + \Sigma cx_{tj}I^3_{tj} + \ldots + \Sigma ax_{rj}I_{rj} + \Sigma bx_{rj}I^2_{rj} + \Sigma cx_{rj}I^3_{rj} + \ldots$$

where:

j=1-10, represents 10 discrete light sources in the NIR and visible spectrum;

$I_{tj}$=intensity of the light from source j, detected on the transmittance photo-detector;

$I_{rj}$=intensity of the light from source j, detected on the reflectance photo-detector;

CP=coagulation parameter, e.g. Cy(90), RCT, Cy(60); and $ax_{tj}$, $bx_{tj}$, $cx_{tj}$, ... $ax_{rj}$, $bx_{rj}$, $cx_{rj}$, =empirical coefficients, relating the intensities of the light detected to the coagulation property CP.

According to one embodiment, a third order polynomial is used, and only coefficients up to $cx_{tj}$ and $cx_{rj}$ are used.

Typically, values of the empirical coefficients are initially experimentally determined preferably by using a statistical analysis method, such as by performing PLS regression, PCA and/or multivariate component analysis on a large collection of samples where the curd firmness and/or rennet coagulation times are known through standard detection methods. To provide a sufficiently broad database, the samples are typically obtained from several hundred different cows.

Once these coefficients are known they are stored, along with the coagulation parameter value of the sample with which they are associated, as a reference database in the computing system memory for use in measurements of unknown samples. In one embodiment of the present invention, the extraction of the coagulation parameter from an unknown sample of milk is performed by a further statistical analysis method, comparing the measured intensities with the contents of the database, such as may be known from chemometric analysis methods used in the analysis of multiple component chemical reaction dynamics. According to one embodiment of the present invention, the analyzer uses sixteen LED sources 221, such that thirty two measurement signals are obtained from each unknown sample of milk, sixteen from transmission measurements, one from each of the sixteen LED's 221, and sixteen from reflectance or back-scattering measurements, one from each of the sixteen LED's 21. These thirty two measurement signals, each at their known wavelength range, are then related, by the statistical analysis chemometric-type methods, to a large database of stored spectral curves related to various milk coagulation properties. This method of calibration and analysis thus allows the use of inexpensive LED's 221 with their non-uniform wide spectral range as light sources, rather than a more discrete and monochromatic source of light, such as a laser, as is used in some prior art optical fluid analyzers.

According to some embodiments of the present invention, other mathematical and/or statistical methods besides the polynomial method are used to determine a relationship between measurements made and the coagulation properties of the raw milk sample. In one embodiment of the present invention, multi-variate analysis is performed. In another embodiment, PLS regression is implemented. In yet another embodiment, PCA is used. Optionally, other methods are implemented, including for example neural network schemes, genetic algorithms, non-linear PCA, Multiple Linear Regression (MLR) and cluster analysis. One or more algorithms may be selected based on precision, stability and processing power and/or time required for implementation.

According to some embodiments, more than one analysis method is used and the results are compared. According to some embodiments of the present invention, different algorithms and/or analysis methods may be implemented for predicting different properties of milk.

Although embodiments of the present invention have been described using sixteen LEDs, the system and methods described herein are not confined to using sixteen LEDs and may be implemented using more or fewer than sixteen LEDs. Additionally, the system and methods described herein are not limited to using LEDs with the wavelengths of the LEDs as described herein. Furthermore, more or less than thirty two measurement signals may be used in the defined polynomial. For example 48 measurement signals may be used, e.g. 16 from transmission measurements, 16 from reflectance measurements, and 16 from backscattering measurements.

Results of these concentration analyses for all of the milk components detected may be printed or displayed on output unit 234 and transferred to a herd management system for analysis. According to some embodiments of the present invention, output unit 234 is integral to control system 114.

Figure 4:
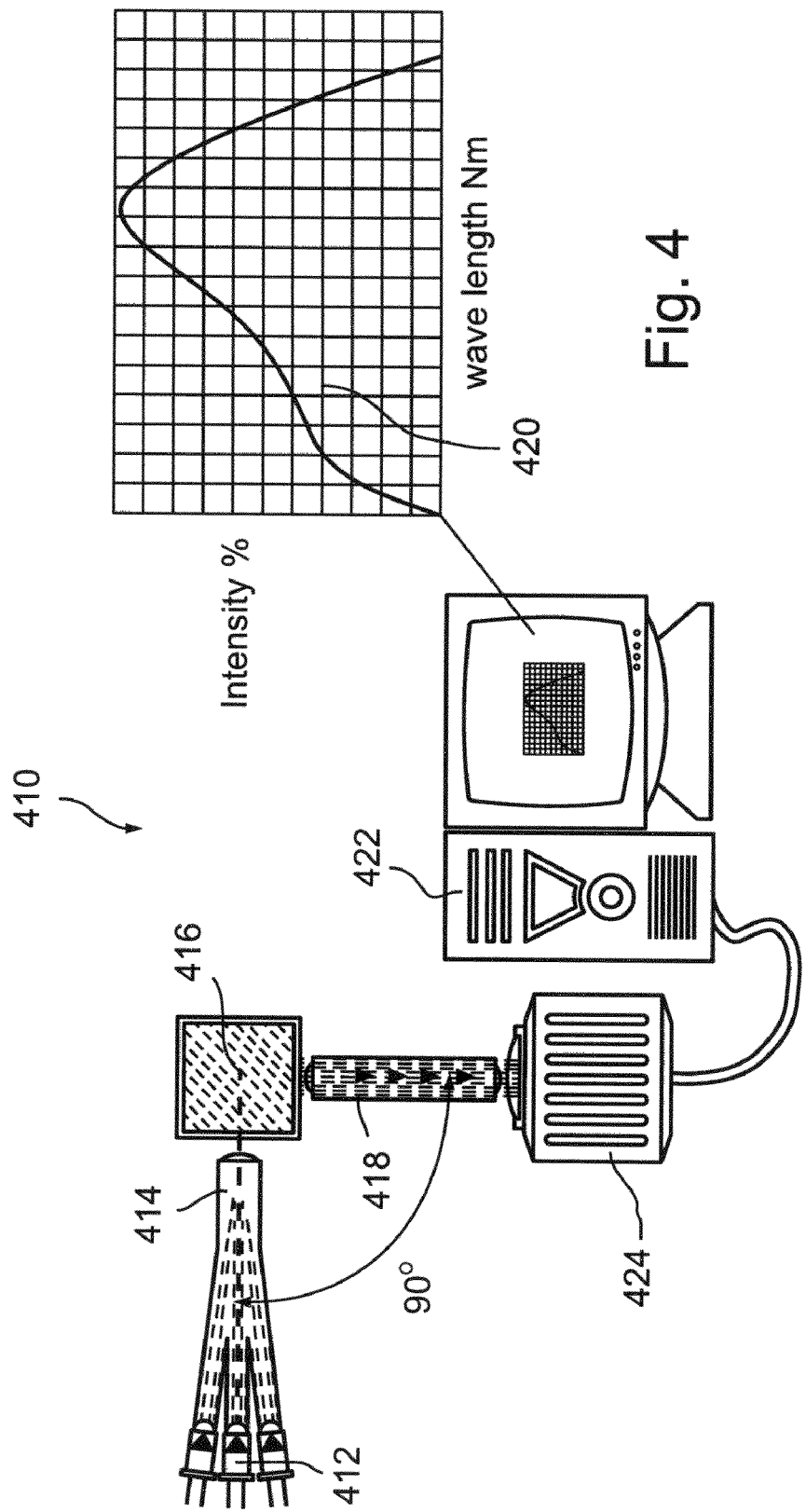

Reference is now made to FIG. 4 showing a schematic diagram a fluorescence measurement system to be used for on-line analysis of coagulation properties of raw milk according to some embodiments of the present invention. According to some embodiments of the present invention, one or more discrete light sources 412 consecutively illuminate and excite a milk sample in a sampling chamber 416 through a light guide 414. According to some embodiments of the present invention, light sources 412 illuminate at pre-selected wavelengths between 290 nm and 430 nm. In some exemplary embodiments, sampling chamber 416 may be similar to sampling chamber 218. According to some embodiments of the present invention, fluorescent light emitted at 90 degrees is collected via a light guide 418 and a lattice and/or spectrometer 424 records the emission spectra. According to some embodiments of the present invention, spectra data, e.g. spectra data 420, is used to calculate the coagulation properties using a computing unit 422. According to some embodiments of the present invention, functionality of computing unit 422 may be embedded in control system 114 and/or analyzer 124.

Typically, there are many fluorescing substances in milk such as Triptophan and other aromatic amino-acids, Vitamin A, FAD, FADH, NaDH, Xantine-oxidase and others. The fluorescence spectrum for each irradiating wavelength is affected by components and characteristics of particular raw milk samples. The present inventors have found that these fluorescence spectra may be used to determine coagulation properties of raw milk as well as other milk components such as fat, protein, casein and somatic cell count.

Figure 5:
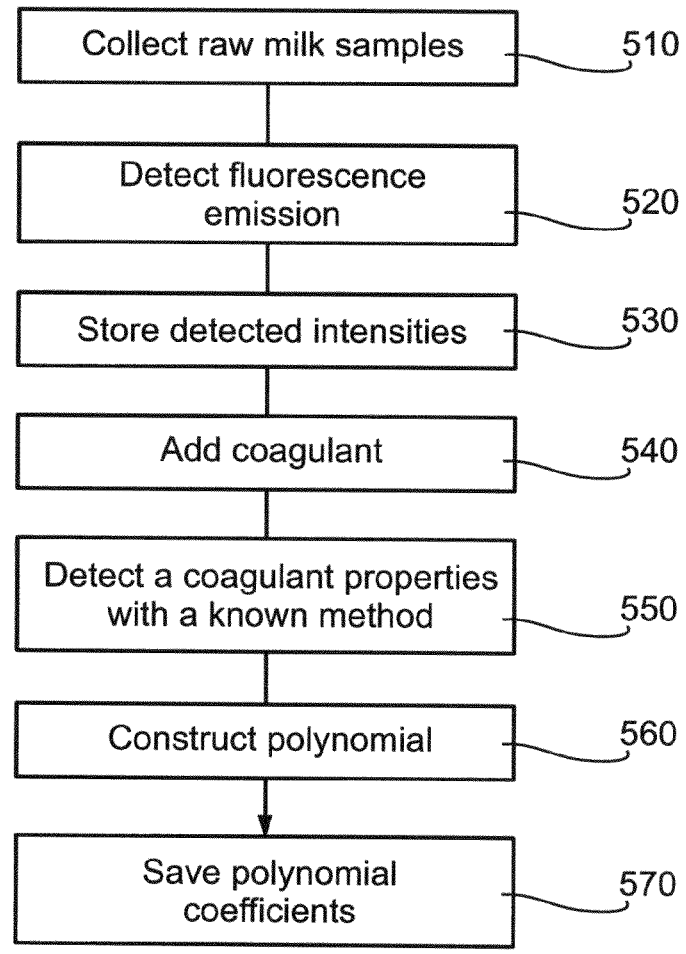

Reference is now made to FIG. 5 showing simplified flow chart describing an exemplary method for determining relationship between detected intensities from a fluorescence measurement system and at least one coagulant property of raw milk according to some embodiments of the present invention. According to embodiments of the present invention, raw milk samples are collected from a large number of cows and from different points in time during the milking session (block 510). According to some embodiments of the present invention fluorescence is performed according to determine fluorescence emissions for the different samples collected (block 520). Detected fluorescence emissions from the samples are stored (block 530). In some exemplary embodiments, a coagulant, e.g. rennet, is added to each of the samples collected (block 540). One or more known methods for determining one or more coagulant property may be determined (block 550). In one example, a curd firmness parameter is determined using an optigraph. For example curd firmness after 90 minutes, Cy(90) is determined. In one example the parameter RCT is determined using known methods. More than one parameter may be determined and more than one known method may be implemented to determine each of the parameters.

According to some embodiments of the present invention, coagulation properties of raw milk is defined by fitting the fluorescence emissions detected from each of the light sources to a polynomial expression for a defined coagulation parameter in terms of the fluorescence emissions detected and one or more empirical coefficients (block 560). According to embodiments of the present invention, empirical coefficients are determined by a statistical analysis of the fluorescence emissions for each of the light sources 412 and from a plurality of samples of the fluid having known coagulation parameters. Once determined, the empirical coefficients are preferably stored in a database (block 570) and may be used to determine coagulation parameters of future samples of raw milk in real time. According to embodiments of the present invention statistical analysis performed for construction of the polynomial may be similar to that described in reference to NIR spectroscopy analysis. According to some embodiments of the present invention, multi-variate analysis, PLS regression and/or PCA are used to determine coagulation properties of milk from the NIR spectroscopy analysis of milk samples.

Figure 6:
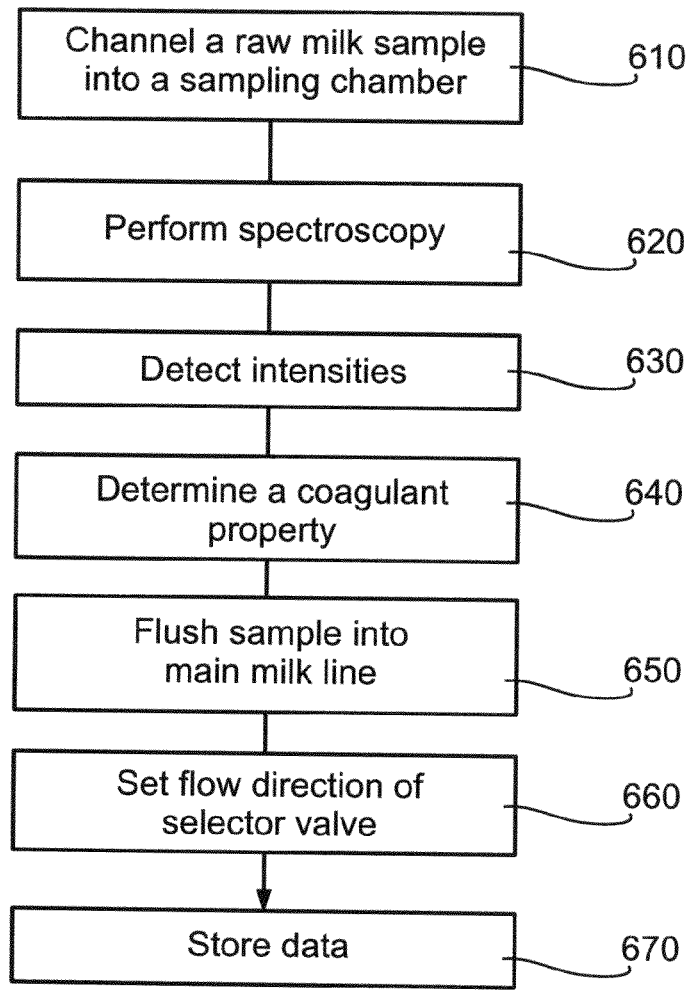

Reference is now made to FIG. 6 showing a simplified flow chart describing an exemplary method for on-line analysis and channeling of raw milk based on coagulation properties according to some embodiments of the present invention. According to some embodiments of the present invention, optical analysis systems such as described in reference to FIGS. 2 and 4 may be implemented for performing on-line analysis and channeling of raw milk based on its coagulation properties. According to some embodiments of the present invention, during a milking session, a raw milk sample is channeled into a sampling chamber (block 610). Spectral analysis in the NIR and/or fluorescence spectra is performed (block 620). Intensities and/or emissions are detected (block 630). One or more coagulant properties are determined based on a pre-defined polynomial expression including a plurality of pre-determined empirical coefficients. The milk sample is flushed into the main milk line and/or replaced by a new upstream sample (block 650) and the direction of the selection valve is set to channel the current milk flow to a selected destination, e.g. milk line and/or milk vat (block 660). Data of coagulation properties as well as other data is optionally stored (block 670).

In one exemplary embodiment, the predicted coagulation parameter is Cy(90) and based on this prediction, milk flow is distributed through three separate lines. For example Cy(90) <4 will be channeled through a line and/or into a vat to be used for drinking; 4>Cy(90)<10 will be channeled for soft cheese, e.g. cottage cheese and yoghurt, Cy(90)>10 will be channeled for dry cheese, e.g. cheddar cheese, farmagiano.

Typically, Cy(90) increases over a milking session due to an increase in the fat concentration of milk over the milking session. In some exemplary embodiments of the present invention, and depending the coagulation properties of individual cows, a first portion of milk excreted during a milking session is channeled through a line and/or into a vat to be used for drinking, a middle portion of milk excreted during the milking session is channeled through a line and/or into a vat to be used for soft cheese, and a final portion of milk during the milking session is channeled through a line and/or into a vat to be used for hard cheeses. The portion of the milking session used for the different products depends on on-line predicted coagulation properties of the milk, e.g. prediction of Cy(90). In one exemplary embodiment, milk from cows that produce milk with a relatively high coagulation ability, is only used for cheese production while milk from cows that produce milk with a relatively low coagulation ability is only used for drinking and/or soft cheese production. According to some embodiments of the present invention, milk from cows having an elevated SCC count, e.g. detected based on on-line prediction of Cy(90), is channeled to a separate line and/or vat.

According to some embodiments of the present invention, detection of reduction of a value of one or more detected coagulation properties is used as an indication to terminate the milking session. According to some embodiments of the present, invention, termination of the milking session is performed automatically based on analysis of one or more recorded parameters during the milking session.

Reference is now made to FIG. 7 showing a graph of sample results obtained from three different polynomials used to predicate values of curd firmness using an on-line NIR spectroscopy system according to some embodiments of the present invention. The coagulation property measured is the curd firmness after 90 minutes Cy(90). The X axis represents results measured by an optigraph while the Y axis represents predicted values of Cy(90) based on results measured over one day by NIR spectroscopy system described inter alia in reference to FIGS. 2-3. Each of the lines in FIG. 7 represents the results of a model created from one set of data obtained over a day and applied to predict coagulation parameters obtained over two other days. For example, linear curve 710 shows measured and predicted values of Cy(90) from samples collected on Day 2 and Day 3, based on a polynomial defined from samples collected on Day 1. Likewise, linear curve 720 shows measured and predicted values of Cy(90) from samples collected on Day 1 and Day 3 based on a polynomial defined from samples collected on Day 2. Linear curve 730 shows measured and predicted values of Cy(90) from samples collected on Day 1 and Day 2 based on a polynomial defined from samples collected on Day 3. According to some embodiments of the present invention, a stable model is defined when substantially all the lines, e.g. the three lines 710, 720 and 730, substantially overlap and/or when the standard deviation between the different models is less than the standard deviation between different samples of a single model. According to some embodiments of the present invention, the number of samples, e.g. cows, used to define the model is increased until a stable model is determined. In some exemplary embodiments, approximately 500-2000 milking sessions, e.g. 1000 milking sessions are used to define the statistical model for predicating Cy(90) parameter, typically obtained from 500 cows or more.

Reference is now made to FIGS. 8A and 8B showing sample results obtained when comparing measured and predicated values of curd firmness and rennet coagulation time respectfully for values predicted with an on-line fluorescence system according to some embodiments of the present invention. In FIG. 8A, the property measured is the Curd Firmness after 90 minutes Cy(90) and in FIG. 8B, the property measured is RCT. The X axis represents results measured by an optigraph while the Y axis represents results predicted by the fluorescence emission of Triptophan (excitation at 290 nm) spectra model described inter alia in reference to FIGS. 4-5.

Although embodiments of the present invention have been described based on performing spectral analysis to predict coagulation properties of milk on-line, other measuring techniques may be equally applied including ultrasound, electrical conductance, and chemosensors.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A method for on-line channeling of milk based on predicted future coagulation properties, the method comprising:
   sampling raw milk from a milk line to obtain a raw milk sample from the raw milk, wherein the milk line directly connects a milking station to a plurality of collection points;
   performing spectral analysis of one or more of optical transmission, optical reflectance, scatter and fluorescence on the raw milk sample;
   predicting at least one future coagulation parameter on-line based on the spectral analysis; and
   channeling the raw milk from the milk line directly to one of a plurality of collection points based on the at least one future coagulation parameter predicted.

2. The method according to claim 1, wherein the spectral analysis is implemented with NIR spectroscopy.

3. The method according to claim 1, wherein the spectral analysis is implemented with visible light spectroscopy.

4. The method according to claim 1, wherein the spectral analysis is performed using a plurality of LED, each configured for illuminating the raw milk sample at a different wavelength within the range to be used for the measurement.

5. The method according to claim 4, wherein the range is between 365 nm to 950 nm.

6. The method according to claim 1, wherein the spectral analysis is performed using one or more detectors to detect light transmitted through the raw milk sample.

7. The method according to claim 1, wherein the spectral analysis is performed using one or more detectors to detect light reflected from the raw milk sample.

8. The method according to claim 1, wherein the spectral analysis is performed using one or more detectors to detect light scatter from the raw milk sample.

9. The method according to claim 1, wherein the spectral analysis is implemented with fluorescence spectroscopy.

10. The method according to claim 9, wherein the spectral analysis is performed using a plurality of light sources having pre-selected wavelengths between 290 nm and 430 nm.

11. The method according to claim 9, comprising detecting light scattered at substantially 90 degrees.

12. The method according to claim 1, wherein prediction is based on pre-stored empirical data.

13. The method according to claim 1, comprising determining a coagulation property of the raw milk sample based on a pre-defined polynomial including empirical coefficients obtained from statistical analysis of a large number of test samples from different cows and from different periods over a milking session having a known coagulation property.

14. The method according to claim 13, wherein the known coagulation property is determined from optical measurements of each of the test samples after adding rennet to the test samples.

15. The method according to claim 1, wherein the sampling is performed on pulsating milk flow.

16. The method according to claim 15, wherein the spectral analysis is performed a plurality of times on each sample.

17. The method according to claim 1, wherein the at least one future coagulation parameter is selected form a group including: Cy(90), Cy(60), and RCT.

18. The method according to claim 1, wherein the analysis on the raw milk sample does not involve adding a coagulant to the milk.

19. The method according to claim 1, wherein the channeling is performed automatically and without human intervention.

20. The method according to claim 1, wherein the channeling is performed from a milk station of an individual cow.

21. The method according to claim 1, comprising channeling milk that is predicted to later yield a curd firmness below a defined threshold for drinking and channeling milk determined to later yield a curd firmness above the defined threshold for cheese production.

22. The method according to claim 1, comprising flushing the raw milk sample together with the raw milk in the milk line to the one of the plurality of collection points based on the at least one future coagulation parameter predicted.

23. A system for on-line channeling of milk according to a predicted future coagulation property of raw milk comprising:
- a milk line configured to provide direct milk flow between a milking station and a plurality of collection points;
- a sampling chamber configured for receiving pulsating milk samples from the milk line;
- an analyzer configured for determining at least one optical property of a sample of raw milk flowing through the milk line;
- a processor operative to estimate a future coagulation property that the raw milk will have based on the optical data; and
- a controller that receives the estimate from the processor and directly channels the raw milk in the flow line to one of the plurality of collection points responsive to the estimated coagulation property.

24. The system according to claim 23, wherein the analyzer is an NIR spectroscopy analyzer.

25. The system according to claim 23, wherein the analyzer includes a visible light spectroscopy analyzer.

26. The system according to claim 23, wherein the analyzer is a fluorescence spectroscopy analyzer.

27. The system according to claim 23, comprising a memory unit for storing empirical coefficients relating output from the analyzer to the future coagulation property of the sample based on a defined polynomial function.

28. The system according to claim 27, wherein the empirical coefficients are obtained from statistical analysis of a large number of test samples from different cows and from different periods over a milking session having a known coagulation property.

29. The system according to claim 23, wherein the future coagulation property predicted is a parameter selected from the group comprising: Cy(90), Cy(60), and RCT.

30. The system according to claim 23, wherein the controller is configured for channeling milk to the one of the plurality of collection points responsive to the predicted coagulation property at a resolution of each pulsating sample of milk.

31. The system according to claim 23, wherein the controller is configured for channeling milk to the one of the plurality of collection points responsive to the predicted coagulation property at a resolution of approximately once every 2 seconds.

32. The system according to claim 23, wherein the analyzer is configured for performing analysis on the sample of raw milk without adding a coagulant to the sample of raw milk.

33. The system according to claim 23, wherein the sampling chamber is configured to flush the milk samples into the milk line.

34. A method for predicting future coagulation properties of raw milk, the method comprising:
- performing spectral analysis of one or more of optical transmission, optical reflectance, scatter and fluorescence on the raw milk without adding a coagulant; and
- predicting on-line during milking at least one coagulation parameter that the raw milk will have after a coagulant is added to the raw milk based on the spectral analysis.

35. The method according to claim 34, wherein the spectral analysis is implemented with NIR spectroscopy.

36. The method according to claim 34, wherein the spectral analysis is implemented with visible light spectroscopy.

37. The method according to claim 34, wherein the spectral analysis is implemented with fluorescence spectroscopy.

38. The method according to claim 34, wherein prediction is based on pre-stored empirical data.

39. The method according to claim 34, wherein the predicting is based on a pre-defined polynomial including empirical coefficients obtained from statistical analysis of a large number of test samples from different cows and from different periods over a milking session having a known coagulation property.

40. The method according to claim 39, wherein the known coagulation property is determined from optical measurements of each of the test samples after adding rennet to the test sample.

41. The method according to claim 34, wherein the spectral analysis is performed a plurality of times on each sample.

42. The method according to claim 34, wherein the at least one coagulation parameter is selected form a group including: Cy(90), Cy(60), and RCT.

43. A system for on-line analysis to predict at least one future coagulation property that milk will have after a coagulant is added to the milk comprising:
- a sampling chamber configured for receiving pulsating milk samples on-line from the milk line;
- an analyzer configured for determining at least one property of a milk sample in the sampling chamber; and
- a processor operative to estimate on-line a future coagulation property that the milk sample will have after a coagulant is added to the milk sample based on the at least one property and pre-stored empirical data relating the at least one property to a future coagulation property of the milk.

44. The system according to claim 43, wherein the analyzer is configured for performing analysis on the milk sample without adding a coagulant to the sample of raw milk.

45. The system according to claim 43, wherein the analyzer is configured for determining at least one optical property of the milk sample.

46. The system according to claim 43, wherein the coagulation property is determined by a parameter selected from the group comprising: Cy(90), Cy(60), and RCT.

47. The system according to claim 43, comprising a memory unit for storing empirical coefficients relating output from the analyzer to at least one coagulation property of the milk sample based on a defined polynomial function.

48. The system according to claim 47, wherein the empirical coefficients are obtained from statistical analysis of a large number of milk samples from different cows and from different periods over a milking session having a known coagulation property.

49. The system according to claim 43, wherein the sampling chamber is configured for flushing the milk samples into the milk line.

* * * * *